United States Patent [19]
Rosen et al.

[11] Patent Number: 5,688,495
[45] Date of Patent: Nov. 18, 1997

[54] TOPICAL DEODORANT COMPOSITIONS

[76] Inventors: Steven E. Rosen, 2150 SW. 90th Ave. Unit A, Ft. Lauderdale, Fla. 33324; Robert Lee Brown, 3923 Evergreen, Irving, Tex. 75061

[21] Appl. No.: 593,401

[22] Filed: Jan. 29, 1996

Related U.S. Application Data

[63] Continuation-in-part of Ser. No. 039,843, Mar. 30, 1993.

[51] Int. Cl.$^6$ .................. A61K 7/32; A61K 7/00
[52] U.S. Cl. .............. 424/65; 424/400; 424/401; 424/DIG. 5
[58] Field of Search ............... 424/65, 400, 401, 424/DIG. 5; 572/1

[56] References Cited

U.S. PATENT DOCUMENTS

| | | |
|---|---|---|
| 3,136,696 | 6/1964 | Harrison . |
| 4,199,576 | 4/1980 | Reller et al. ............... 424/230 |
| 4,946,870 | 8/1990 | Partain, III ................ 574/777 |
| 5,034,221 | 7/1991 | Rosen ........................ 424/73 |
| 5,204,093 | 4/1993 | Victor ......................... 424/73 |
| 5,223,267 | 6/1993 | Nichols ..................... 424/489 |

*Primary Examiner*—Shelley A. Dodson
*Attorney, Agent, or Firm*—Crutsinger & Booth

[57] ABSTRACT

Topical deodorant and compositions are provided. The deodorant compositions include in the range of about 20 to about 80 percent by weight of an acetylsalicylic acid solution and in the range of about 20 to about 80 percent by weight of a waxy carrier. The acetylsalicylic acid solution has acetylsalicylic acid in the range of between about 5 percent by weight per unit volume of a solvent mixture up to saturation of the solvent mixture. This solvent mixture consists essentially of propylene glycol in the range of about 5 to 15 percent by volume, glycerin in the range of about 1 to 10 percent by volume, and the balance of the solvent mixture made up with one or more solvents selected from the group consisting of isopropyl alcohol, water, and ethanol, the balance of the solvent mixture comprising at least 50 percent by volume isopropyl alcohol. The waxy carrier preferably includes cetyl alcohol and sodium stearate. Thus, the composition has a waxy consistency for ease of application to the skin for antiperspirant purposes.

9 Claims, No Drawings

TOPICAL DEODORANT COMPOSITIONS

This is a continuation-in-part of copending U.S. application Ser. No. 039,843 filed Mar. 30, 1993 for "Topical Compositions and Methods for Treating Pseuodfolliculitis Barbae."

BACKGROUND OF THE INVENTION

Antiperspirant formulations typically rely on the use of alum, aluminum zirconium tetrachlorohdrex gly, and aluminum chlorohydrate as the active ingredients. Although aluminum chlorohydrate based products are highly effective antiperspirants, some people are concerned that with daily use, the aluminum chlorohydrate is absorbed into the body, which might be detrimental to health. The aluminum based compounds may react in the body in undesired ways.

SUMMARY OF THE INVENTION

According to the invention, new compositions are provided for topical application to the skin for deodorant purposes. The new compositions include acetylsalicylic acid in a suitable carrier for application to the skin. It has been discovered that acetylsalicylic acid can be a highly effective active ingredient for deodorant and formulations, which avoids the need to use aluminum chlorohydrate or other metal compounds.

The improved deodorant compositions can include, if desired, effective amounts of other ingredients such as coloring agents, fragrance, and medications to further soothe and aid in healing the skin.

It is an object of the invention to provide an improved deodorant that does not require aluminum chlorohydrate. These and other objects and advantages of the invention will become apparent to those skilled in the art upon reading the following detailed description of preferred embodiments.

DETAILED DESCRIPTION OF PREFERRED EMBODIMENTS

According to the presently most preferred embodiment of the invention, the deodorant compositions are made with an acetylsalicylic acid solution mixed with a waxy carrier.

For the acetylsalicylic acid solution, the acetylsalicylic acid is present in the range of between about 5 percent by weight per unit volume of a solvent mixture up to saturation of the solvent mixture.

The solvent mixture preferably comprises propylene glycol in the range of about 5 to 15 percent by volume, glycerine in the range of about 1 to 10 percent by volume, and the balance of the volume substantially made up with isopropyl alcohol alone or a solution comprising at least 50 percent of isopropyl alcohol. For example, the isopropyl alcohol can be in a solution with water or ethanol, provided that the polarity of the resulting composition is not so high that the acetylsalicylic acid would readily precipitate from solution at ordinary room temperatures. More preferably, the acetylsalicylic acid should not precipitate at temperatures above about 50° F.

In more preferred embodiments of the invention, the acetylsalicylic acid preferably is present in the range of about 10 percent by weight per unit volume of the solvent mixture up to saturation of the solvent mixture. Furthermore, the propylene glycol preferably is present in the solvent mixture in the range of about 10 to 15 percent by volume. The glycerine is preferably present in the solvent mixture in the range of about 2 to 4 percent by volume. And the balance of the solvent mixture preferably is substantially made up with isopropyl alcohol alone or a solution of isopropyl alcohol and water, provided that the isopropyl alcohol is at least about 70 percent by volume of the solution of isopropyl alcohol and water.

In a most preferred embodiment of the invention, which appears to be the most effective for deodorant purposes, the acetylsalicylic acid is present in the range of about 15 percent by weight per trait volume of the solvent mixture up to saturation of the solvent mixture and the solvent mixture comprises propylene glycol in about 10 percent by volume, glycerine in about 2 percent by volume, and the balance of the volume substantially made up with isopropyl alcohol alone or a solution of isopropyl alcohol and water, provided that the isopropyl alcohol is at least about 70 percent by volume of the solution of isopropyl alcohol and water. Where the isopropyl alcohol is about 70 percent by volume of the solution of isopropyl alcohol and water, the saturation concentration of the acetylsalicylic acid in this solvent mixture is about 18 percent by weight per unit volume.

In preparing the composition, it can be helpful to gently warm the solvent mixture of propylene glycol, glycerine, isopropyl alcohol, and water (if any) to assist the acetylsalicylic acid in completely dissolving in the solvent mixture. It has been observed that the typical consumer tends to prefer a product that is homogeneous in appearance and without any precipitate. The acetylsalicylic acid is virtually insoluble in water or water based substances. Thus, aloe vera, for example, while it is soothing to the skin, tends to quickly hydrolyze acetylsalicylic acid. The hydrolysis of the acetylsalicylic acid would substantially and undesirably shorten the shelf life of the product.

After the acetylsalicylic acid is dissolved in the solvent mixture as just described, the acetylsalicylic acid solution is then further mixed with a waxy carrier to provide an deodorant composition. According to the presently most preferred embodiment of the invention, the waxy carrier is a combination of cetyl alcohol and sodium stearate. Thus, the composition provides an appropriate deodorant delivery system. For example, according the presently most preferred embodiment of the invention, 25 grams of the acetylsalicylic acid and solvent mixture is then mixed with 30 grams cetyl alcohol and 5 grams sodium stearate. Thus, the presently most preferred ratio is 25:30:5 (acetylsalicylic acid solution: cetyl alcohol: sodium stearate) by weight.

Propylene glycol (1,2-propanediol; methylene glycol) appears to be an important solvent carrier for the acetylsalicylic acid. Furthermore, it is a moisturizer and produces a pleasant emollient feel when applied to the skin. Propylene glycol has the additional benefit of being a mild germicide. However, in excessive concentrations the germicidal properties can irritate sensitive facial skin.

Glycerine (glycerol; 1,2,3-propanetriol) is a mild astringent that causes increased blood flow to the skin and allows the propylene glycol to carry the acetylsalicylic acid into the epidermis and hair follicles. Excessive amounts of glycerine could allow the propylene glycol to penetrate below the epidermis, which would be undesirable.

Isopropyl alcohol (isopropanol; 2-propanol) or a solution of isopropyl alcohol with ethanol and/or water serves as a bulk solvent for the other ingredients of the composition. Isopropyl alcohol also serves to dissolve oils and grease thus cleaning the skin and permitting more intimate contact of the other ingredients with the skin. Isopropyl alcohol is less dehydrating to the skin than ethanol, and because it is less polar, it is a better solvent for the acetylsalicylic acid. It is anticipated, however, that some ethanol in the composition would not adversely effect the effectiveness the composition.

Cetyl alcohol (1-hexadecanol, normal) is a fatty alcohol that provides a waxy carrier. Sodium stearate is a white powder with fatty characteristics.

Acetylsalicylic acid, propylene glycol, glycerin, isopropyl alcohol, cetyl alcohol, and sodium stearate are all generally recognized as safe for topical application to the skin or for cosmetic purposes.

In a presently most preferred embodiment, an effective amount of a coloring agent such as FD&C Blue No. 6 is added to the composition to effect a pleasing blue color to the product. Furthermore, fragrance such as citrus or other perfume is also added to create a pleasant smell, which can help mask undesired body odor.

The deodorant compositions according to the invention have a waxy consistency, and with sufficient proportion of waxy carrier can be formed into a stick for convenient application to the skin. Thus, the compositions can be applied in a thin layer to the desired body areas, particularly the under arms, by drawing the surface of the stick across the skin.

The examples described above are only exemplary. Even though numerous characteristics and advantages of the present inventions have been set forth in the foregoing description, together with our understanding of the function of the components, the disclosure is illustrative only, and changes may be made in the composition within the principles of the inventions to the full extent indicated by the broad general meaning of the terms used in the attached claims. The limits of the inventions and the bounds of the patent protection are measured by and defined in the following claims.

Having described the inventions, what is claimed is:

1. A composition for use as a deodorant consisting essentially of:

in the range of about 20 to about 80 percent by weight of an acetylsalicylic acid solution having acetylsalicylic acid in the range of between about 5 percent by weight per unit volume of a solvent mixture up to saturation of said solvent mixture, said solvent mixture consisting essentially of propylene glycol in the range of about 5 to 15 percent by volume, glycerine in the range of about 1 to 10 percent by volume, and the balance of said solvent mixture made up with one or more solvents selected from the group consisting of isopropyl alcohol, water, and ethanol, said balance of said solvent mixture comprising at least 50 percent by volume isopropyl alcohol; and in the range of about 80 to about 20 percent by weight of a waxy carrier.

2. A composition according to claim 1, wherein said waxy carrier consists of essentially of cetyl alcohol and sodium stearate.

3. A composition according to claim 2, wherein said acetylsalicylic acid solution is about 40 percent by weight of the composition and said waxy carrier is about 60 percent by weight of the composition.

4. A composition according to claim 3, wherein said waxy carrier consists essentially of:

about 15 percent by weight of cetyl alcohol; and about 85 percent by weight of sodium stearate.

5. A composition according claim 1, wherein said acetylsalicylic acid is present in the more preferred range of about 10 percent by weight per unit volume of said solvent mixture up to saturation of said solvent mixture.

6. A composition according to claim 1, wherein said propylene glycol is present in said solvent mixture in the more preferred range of about 10 to 15 percent by volume.

7. A composition according to claim 1, wherein said glycerine is present in said solvent mixture in the more preferred range of about 2 to 4 percent by volume.

8. A composition according to claim 1, further consisting essentially of: an effective amount of coloring agent to change the appearance of the composition.

9. A composition according to claim 1, further consisting essentially of: an effective amount of fragrance to provide a pleasant smell to the composition.

* * * * *

UNITED STATES PATENT AND TRADEMARK OFFICE
CERTIFICATE OF CORRECTION

PATENT NO. : 5,688,495
DATED : November 18, 1997
INVENTOR(S) : Steven E. Rosen, et. al.

It is certified that error appears in the above-identified patent and that said Letters Patent is hereby corrected as shown below:

In the Abstract, line 11 the word "glycerin" should be -- glycerine --;

In the Abstract. line 19 delete the word "of";

In Column 1, line 25 delete the word "and";

In Column 2, line 9 the word "trait" should be -- unit --;

In Column 2, line 35 the word "an" should be -- a --;

In Column 3, line 2 after the word "effectiveness" insert the word -- of --;

In Column 3, line 7 the word "glycerin" should be -- glycerine --;

Signed and Sealed this

Twenty-second Day of September, 1998

Attest:

BRUCE LEHMAN

*Attesting Officer*  *Commissioner of Patents and Trademarks*